(12) United States Patent
Ascheman

(10) Patent No.: US 9,274,060 B1
(45) Date of Patent: Mar. 1, 2016

(54) METHODS FOR TRANSMEMBRANE MEASUREMENT OF OXYGEN CONCENTRATION AND MONITORING CHANGES IN OXYGEN CONCENTRATION WITHIN A SPACE ENCLOSED BY A MEMBRANE EMPLOYING A PHOTOLUMINESCENT TRANSMEMBRANE OXYGEN PROBE

(71) Applicant: Timothy A. Ascheman, Elk River, MN (US)

(72) Inventor: Timothy A. Ascheman, Elk River, MN (US)

(73) Assignee: MOCON, INC., Minneapolis, MN (US)

( * ) Notice: Subject to any disclaimer, the term of this patent is extended or adjusted under 35 U.S.C. 154(b) by 0 days.

(21) Appl. No.: 14/461,819

(22) Filed: Aug. 18, 2014

Related U.S. Application Data

(62) Division of application No. 13/349,953, filed on Jan. 13, 2012, now abandoned.

(60) Provisional application No. 61/432,310, filed on Jan. 13, 2011.

(51) Int. Cl.
*G01N 33/00* (2006.01)
*G01N 21/25* (2006.01)
*G01N 21/17* (2006.01)
*G01N 21/00* (2006.01)
(Continued)

(52) U.S. Cl.
CPC .............. *G01N 21/763* (2013.01); *G01N 33/00* (2013.01); *G01N 2021/757* (2013.01); *Y10T 436/20* (2015.01); *Y10T 436/207497* (2015.01); *Y10T 436/209163* (2015.01)

(58) Field of Classification Search
CPC ........ G01N 33/00; G01N 21/00; G01N 21/17; G01N 21/25; Y10T 436/00; Y10T 436/20; Y10T 436/207497; Y10T 436/209163
USPC .......... 436/138, 135, 127; 73/1.06, 1.02, 1.01
See application file for complete search history.

(56) References Cited

U.S. PATENT DOCUMENTS 3,138,937 A   6/1964  Parkinson et al.
3,612,866 A   10/1971 Stevens
(Continued)

FOREIGN PATENT DOCUMENTS

JP      2004075155 A    3/2004
WO       9219150 A1    11/1992
(Continued)

OTHER PUBLICATIONS

Lee, Sang-Kyung et al., "Photoluminescent Oxygen Sensing on a Specific Surface Area Using Phosphorescence Quenching of Pt-Pophyrin", Analytical Sciences, Department of Bioengineering, Tokyo Institute of Technology, pp. 535-540, Aug. 1997, vol. 13.
(Continued)

*Primary Examiner* — Christine T Mui
(74) *Attorney, Agent, or Firm* — Sherrill Law Offices, PLLC

(57) ABSTRACT

Measuring oxygen concentration and monitoring changes in oxygen concentration within an enclosed space by applying a transmembrane photoluminescent oxygen probe to the external surface of the membrane forming the enclosed space, wherein the transmembrane photoluminescent oxygen probe has an oxygen impermeable support layer carrying a spot of an oxygen-sensitive photoluminescent dye and a layer of a pressure-sensitive adhesive on a first major surface of the support layer.

10 Claims, 1 Drawing Sheet

(51) Int. Cl.
  *G01N 21/76* (2006.01)
  *G01N 21/75* (2006.01)

(56) References Cited

U.S. PATENT DOCUMENTS

| | | | |
|---|---|---|---|
| 4,476,870 | A | 10/1984 | Peterson et al. |
| 4,784,811 | A | 11/1988 | Hirschfeld |
| 4,810,655 | A | 3/1989 | Khalil et al. |
| 4,947,850 | A | 8/1990 | Vanderkooi et al. |
| 5,190,729 | A | 3/1993 | Hauenstein et al. |
| 5,328,823 | A | 7/1994 | Spencer et al. |
| 5,333,609 | A | 8/1994 | Bedingham et al. |
| 5,382,163 | A | 1/1995 | Putnam |
| 5,407,829 | A | 4/1995 | Wolfbeis et al. |
| 5,695,640 | A | 12/1997 | Tseng |
| 5,718,842 | A | 2/1998 | Papkovsky et al. |
| 5,837,865 | A | 11/1998 | Vinogradov et al. |
| 6,074,607 | A | 6/2000 | Slovaccek et al. |
| 6,153,701 | A | 11/2000 | Potnis et al. |
| 6,165,741 | A | 12/2000 | Wilson et al. |
| 6,266,211 | B1 | 7/2001 | Thomas, III et al. |
| 6,328,932 | B1 | 12/2001 | Carter et al. |
| 6,362,175 | B1 | 3/2002 | Vinogradov et al. |
| 6,379,969 | B1 | 4/2002 | Mauze et al. |
| 6,395,555 | B1 | 5/2002 | Wilson et al. |
| 6,689,438 | B2 | 2/2004 | Kennedy et al. |
| 7,138,270 | B2 | 11/2006 | Papkovsky et al. |
| 7,368,153 | B2 | 5/2008 | Barmore et al. |
| 7,534,615 | B2 | 5/2009 | Havens |
| 7,569,395 | B2 | 8/2009 | Havens et al. |
| 7,642,250 | B2 | 1/2010 | Williams |
| 8,173,438 | B1 | 5/2012 | Putnam et al. |
| 2003/0050543 | A1 | 3/2003 | Hartmann |
| 2005/0113658 | A1 | 5/2005 | Jacobson et al. |
| 2005/0159497 | A1 | 7/2005 | Gauthier et al. |
| 2006/0002822 | A1 | 1/2006 | Papkovsky et al. |
| 2006/0201830 | A1 | 9/2006 | Schoen et al. |
| 2007/0041011 | A1 | 2/2007 | Hayden et al. |
| 2007/0072825 | A1 | 3/2007 | Williams |
| 2007/0212789 | A1 | 9/2007 | Havens et al. |
| 2007/0212792 | A1 | 9/2007 | Havens et al. |
| 2008/0051646 | A1* | 2/2008 | Papkovsky et al. ......... 600/329 |
| 2008/0117418 | A1 | 5/2008 | Claps et al. |
| 2008/0148817 | A1 | 6/2008 | Miller et al. |
| 2008/0190172 | A1 | 8/2008 | Jones |
| 2008/0199360 | A1 | 8/2008 | Shahriari |
| 2008/0215254 | A1 | 9/2008 | Leiner et al. |
| 2008/0242870 | A1 | 10/2008 | Meador et al. |
| 2009/0028756 | A1 | 1/2009 | Shahriari |
| 2009/0029402 | A1 | 1/2009 | Papkovsky |
| 2009/0075321 | A1 | 3/2009 | Obeid et al. |
| 2009/0084156 | A1 | 4/2009 | Matsuda et al. |
| 2009/0130700 | A1 | 5/2009 | Ince et al. |
| 2010/0116017 | A1* | 5/2010 | Mayer et al. .................. 73/1.06 |
| 2010/0209693 | A1 | 8/2010 | Hester et al. |
| 2011/0136247 | A1 | 6/2011 | Papkovsky et al. |
| 2012/0129268 | A1 | 5/2012 | Mayer |

FOREIGN PATENT DOCUMENTS

| | | |
|---|---|---|
| WO | 2006095191 A1 | 9/2006 |
| WO | 2007120637 A2 | 10/2007 |

OTHER PUBLICATIONS

Papkovsky, D. et al., "Phosphorescent Sensor Approach for Non-Destructive Measurement of Oxygen in Packaged Foods: Optimisation of Disposable Oxygen sensors and Their Characterization Over a Wide Temperature Range". Department of Biochemistry, National University of Ireland, Analytical Letters, 33 (9), pp. 1755-1777, Feb. 22, 2000.

Austin, J. P. et al., "Opto-electronic systems for addressing Ru Oxygen Sensors: Their Design Optimization and Calibration Process", Invited Paper, Optoelectronics Research Centre, University of Southampton, Southampton S017 IBJ, Oct. 30, 2001.

Eaton, K. et al., "Effect of Humidity on the Response Characteristics of Luminescent PtOEP Thin Film Optical Oxygen Sensors", Sensors and Actuators B, Elseiver Science B. V., vol. 82, pp. 94-104, May 18, 2001.

De Francisci, M. et al., "Real-Time Estimation of Oxygen Concentration in Micro-Nemo-Vessels", Proceedings of the 26th Annual International Conference of the IEEE EMBS, San Francisco, CA, USA, pp. 2231-2234, Sep. 1-5, 2004.

Technical Manual, Grafted Separators, "Freudenberg Grafted Products", Sep. 2006, pp. 1-32.

\* cited by examiner

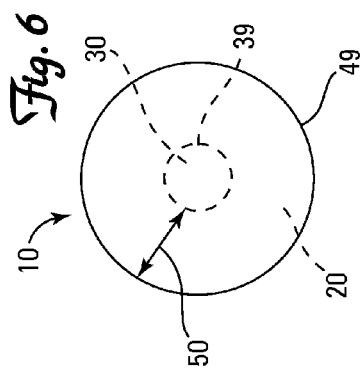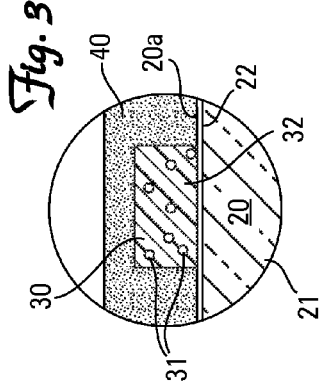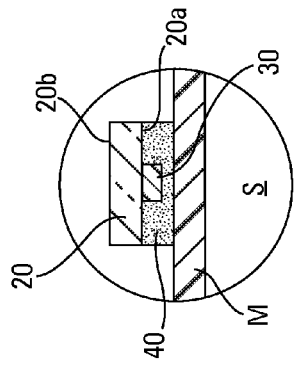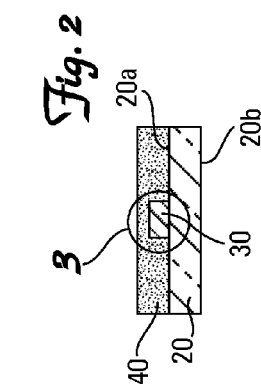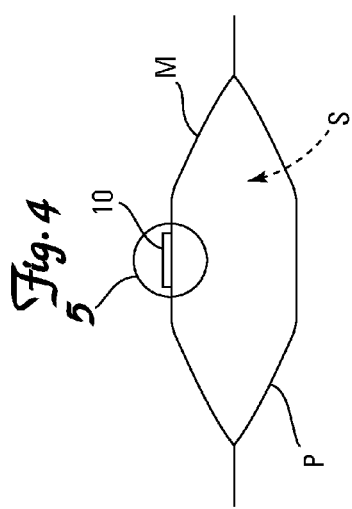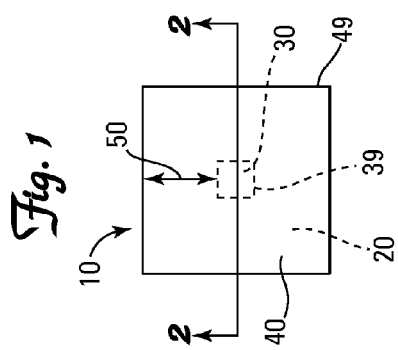

US 9,274,060 B1

METHODS FOR TRANSMEMBRANE MEASUREMENT OF OXYGEN CONCENTRATION AND MONITORING CHANGES IN OXYGEN CONCENTRATION WITHIN A SPACE ENCLOSED BY A MEMBRANE EMPLOYING A PHOTOLUMINESCENT TRANSMEMBRANE OXYGEN PROBE

BACKGROUND

Solid-state polymeric materials based on oxygen-sensitive photoluminescent dyes are widely used as optical oxygen probes. See, for example United States Published Patent Applications 2009/0029402, 2008/8242870, 2008/215254, 2008/199360, 2008/190172, 2008/148817, 2008/146460, 2008/117418, 2008/0051646, 2006/0002822, U.S. Pat. Nos. 7,569,395, 7,534,615, 7,368,153, 7,138,270, 6,689,438, 5,718,842, 4,810,655, and 4,476,870. Such optical probes are available from a number of suppliers, including Presens Precision Sensing, GmbH of Regensburg, Germany, Oxysense of Dallas, Tex., United States, and Luxcel Biosciences, Ltd of Cork, Ireland.

Such probes may be interrogated through many common packaging materials and therefore allow nondestructive measurement of the oxygen concentration within an enclosure by simply incorporating a probe within the packaging, typically adhered to the inside surface of the cover. Unfortunately, there are certain applications where incorporation of such a probe into the packaging is not acceptable—such as packages made from materials that interfere with interrogation of the probe, packages in which the presence of such a probe inside the packaging may be mistakenly perceived by consumers as an undesired contamination of the packaged product, or packages whose per package value or profit margin cannot accommodate the cost of incorporating a probe into every package or tracking those containing a probe when only select packages include a probe.

Hence, a need exists for a probe that can nondestructively sense the oxygen concentration within an enclosure from outside the enclosure.

SUMMARY OF THE INVENTION

A first aspect of the invention is a transmembrane photoluminescent oxygen probe comprising an oxygen impermeable support layer carrying a spot of an oxygen-sensitive photoluminescent dye and a layer of a pressure-sensitive adhesive on a first major surface. The photoluminescent dye is preferably embedded within an oxygen-permeable hydrophobic polymer carrier.

A second aspect of the invention is a method for measuring oxygen concentration within an enclosed space employing an oxygen-sensitive probe according to the first aspect of the invention. The method includes the steps of (A) obtaining a transmembrane photoluminescent oxygen probe according to the first aspect of the invention, (B) adhering the probe to the exterior surface of the membrane with the first major surface of the probe facing towards the membrane, (C) allowing the oxygen concentration in sensible communication with the spot of oxygen-sensitive photoluminescent dye to equilibrate with the oxygen concentration within the space, and (D) ascertaining oxygen concentration within the enclosed space by (i) repeatedly exposing the probe to excitation radiation over time, (ii) measuring radiation emitted by the excited probe after at least some of the exposures, (iii) measuring passage of time during the repeated excitation exposures and emission measurements, and (iv) converting at least some of the measured emissions to an oxygen concentration based upon a known conversion algorithm.

A third aspect of the invention is a method for monitoring changes in oxygen concentration within an enclosed space employing an oxygen-sensitive probe according to the first aspect of the invention. The method includes the steps of (A) obtaining a transmembrane photoluminescent oxygen probe according to the first aspect of the invention, (B) adhering the probe to the exterior surface of the membrane with the first major surface of the probe facing towards the membrane, (C) allowing the oxygen concentration in sensible communication with the spot of oxygen-sensitive photoluminescent dye to equilibrate with the oxygen concentration within the space, (D) ascertaining oxygen concentration within the enclosed space over time by (i) repeatedly exposing the probe to excitation radiation over time, (ii) measuring radiation emitted by the excited probe after at least some of the exposures, (iii) measuring passage of time during the repeated excitation exposures and emission measurements, and (iv) converting at least some of the measured emissions to an oxygen concentration based upon a known conversion algorithm, and (E) reporting at least one of (i) at least two ascertained oxygen concentrations and the time interval between those reported concentrations, and (ii) a rate of change in oxygen concentration within the enclosed space calculated from data obtained in step (D).

A fourth aspect of the invention is a method of preparing a transmembrane photoluminescent oxygen probe according to the first aspect of the invention. The method includes the steps of (A) preparing a coating cocktail which contains the photoluminescent oxygen-sensitive dye and the oxygen-permeable polymer in an organic solvent, (B) applying the cocktail to a first major surface of the oxygen impermeable support layer, (C) allowing the cocktail to dry, whereby a solid-state thin film oxygen-sensitive photoluminescent element is formed on the oxygen impermeable support layer, and (D) applying the layer of pressure-sensitive adhesive onto the first major surface of the oxygen impermeable support layer after the cocktail has dried.

BRIEF DESCRIPTION OF THE DRAWINGS

FIG. 1 is a top view of one embodiment of the invention.

FIG. 2 is a cross-sectional side view of the invention depicted in FIG. 1 taken along line 2-2 with the thickness of each layer grossly enlarged to facilitate viewing of the individual layers.

FIG. 3 is a grossly enlarged cross-sectional side view of a central portion of the invention depicted in FIG. 2 with the thickness of each layer grossly enlarged to facilitate viewing of the individual layers.

FIG. 4 is a side view of the invention depicted in FIG. 1 applied to packaging.

FIG. 5 is a cross-sectional side view of a central portion of the invention depicted in FIG. 4 with the thickness of each layer grossly enlarged to facilitate viewing of the individual layers.

FIG. 6 is a top view of a second embodiment of the invention.

DETAILED DESCRIPTION OF A PREFERRED EMBODIMENT

Definitions

As used herein, including the claims, the term "foodstuff" means any substance suitable for being eaten or drunk by animals, including humans, for nutrition or pleasure, or used as an ingredient in such a substance.

As used herein, including the claims, the phrase "oxygen impermeable" means a material that has an oxygen transmission rate of less than 0.1 $cm^3/m^2$ day when measured in accordance with ASTM D 3985.

Nomenclature
10 Oxygen Probe
20 Oxygen Impermeable Support Layer
20a First Major Surface of Oxygen Impermeable Support Layer
20b Second Major Surface of Oxygen Impermeable Support Layer
21 Structural Substrate
22 Thin Glass Coating
30 Oxygen-Sensitive Photoluminescent Element
31 Oxygen-Sensitive Photoluminescent Dye
32 Polymer Carrier
39 Peripheral Edge of Oxygen-Sensitive Photoluminescent Element
40 Pressure Sensitive Adhesive Layer
49 Peripheral Edge of Pressure Sensitive Adhesive Layer
50 Peripheral Margin
P Hermetically Sealed Packaging
M Packaging Film or Membrane
S Retention Chamber or Space Description Construction and Theory of Operation Referring generally to FIG. 4, the invention is a transmembrane oxygen-sensitive probe or sensor 10 useful for externally optically measuring oxygen concentration within an enclosed space S, such as the retention chamber S of a hermetically sealed package P. Referring generally to FIGS. 1 and 2, the probe 10 includes an oxygen impermeable support layer 20 having first and second major surfaces 20a and 20b, respectively, and carrying both an oxygen-sensitive photoluminescent element 30 and a layer of a pressure-sensitive adhesive 40 on the first major surface 20a.

Without intending to be unduly limited thereby, it is believed that the probe 10 can accurately sense an oxygen concentration at the opposite side of a membrane M to which the probe 10 has been attached (i.e., transmembrane) so long as the rate at which oxygen is exchanged between the photoluminescent element 30 and the environment in communication with the surface of the membrane M to which the probe 10 is attached is at least one and preferably closer to at least two orders of magnitude less than the rate at which oxygen is exchanged between the photoluminescent element 30 and the environment in communication with the surface of the membrane M which is opposite the surface to which the probe 10 is attached. This permits the concentration of oxygen to which the oxygen-sensitive photoluminescent element 30 is exposed to equilibrate with the concentration of oxygen at the opposite side of the membrane M with minimal error introduced by oxygen reaching the oxygen-sensitive photoluminescent element 30 from the environment on the side of the membrane M to which the probe 10 is attached.

Once the probe 10 is adhered to a membrane M, oxygen is exchanged between the photoluminescent element 30 and the environment in communication with the surface of the membrane M to which the probe 10 is attached by diffusion from the backside across the support layer 20 and diffusion from the sides across the adhesive layer 40. Diffusion across the support layer 10 can be minimized by selecting a support layer 10 that is constructed from an oxygen impermeable material (i.e., an extremely low oxygen transmission rate (OTR)). Unfortunately, this same option is not available for minimizing diffusion across the layer of pressure-sensitive adhesive 40 as pressure-sensitive adhesives have a fairly high OTR. Hence, in order to minimize diffusion from the sides of the probe 10, the thickness of the pressure-sensitive adhesive layer 40 should be limited so as to minimize the surface area exposed to the surrounding environment and a sizable margin 50 provided from the edge(s) 49 of the adhesive layer 40 to the edge(s) 39 of the photoluminescent element 30 to maximize the width of the adhesive between the surrounding environment and the photoluminescent element 30.

Referring to FIG. 3, the oxygen-sensitive photoluminescent element 30 includes an oxygen-sensitive photoluminescent dye 31, preferably embedded within an oxygen-permeable polymer carrier 32. In order to minimize any interstitial void volume within the oxygen-sensitive photoluminescent element 30, and thereby speed equilibration of the oxygen concentration in sensible communication with the oxygen-sensitive photoluminescent element 30 with the oxygen concentration on the other side of a membrane M to which the probe 10 is adhered, the oxygen-sensitive photoluminescent element 30 is preferably coated directly onto the support layer 20 so as to form a solid mass.

The oxygen-sensitive photoluminescent dye 31 may be selected from any of the well-known oxygen sensitive photoluminescent dyes 31. One of routine skill in the art is capable of selecting a suitable dye 31 based upon the intended use of the probe 10. A nonexhaustive list of suitable oxygen sensitive photoluminescent dyes 31 includes specifically, but not exclusively, ruthenium(II)-bipyridyl and ruthenium(II)-diphenylphenanothroline complexes, porphyrin-ketones such as platinum(II)-octaethylporphine-ketone, platinum (II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium (III) or osmium(II).

Typically and preferably, the oxygen-sensitive photoluminescent dye 31 is compounded with a suitable oxygen-permeable and hydrophobic polymeric carrier 32. Again, one of routine skill in the art is capable of selecting a suitable carrier 32 based upon the intended use of the probe 10 and the selected dye 31. A nonexhaustive list of suitable polymers for use as the oxygen-permeable hydrophobic carrier 32 includes specifically, but not exclusively, polystyrene, polycarbonate, polysulfone, polyvinyl chloride and some co-polymers.

The support layer 20 is selected to provide sufficient structural integrity to the probe 10 and provide an oxygen impermeable barrier. The support layer 20 also needs to be transparent or translucent to radiation at the excitation and emission wavelengths of the dye 31 in the photoluminescent element 30. Suitable materials include specifically, but not exclusively, glass, polymeric substrates 21 coated with a thin layer of glass 22, laminates containing a layer of EVOH sandwiched between other plastics, and a relatively thick layer (i.e., several mils) of a polymer having a moderate oxygen permeability when employed as a thin film, such as PET, Nylon, PVDC (Saran), etc.

Referring generally to FIGS. 2 and 5, the probe 10 includes a layer of a pressure sensitive adhesive 40 on the first major surface 20a of the support layer 20—the same side as the photoluminescent element 30—for adhering the probe 10 to the surface (unnumbered) of a membrane M—such as the exterior surface of packaging P—that defines an enclosed space or retention chamber S whose oxygen concentration is to be measured. The adhesive 40 may but preferably does not cover the luminescent element 30.

Manufacture

The transmembrane photoluminescent oxygen probe 10 can be manufactured by the traditional methods employed for manufacturing such probes 10. Briefly, the transmembrane photoluminescent oxygen probe 10 can be conveniently manufactured by (A) preparing a coating cocktail (not shown) which contains the photoluminescent oxygen-sensitive dye 31 and an oxygen-permeable carrier polymer 32 in an organic solvent (not shown) such as ethylacetate, (B) applying the cocktail to at least the first major surface 20*a* of the oxygen impermeable support layer 20, (C) allowing the cocktail (not shown) to dry, whereby a solid-state thin film oxygen-sensitive photoluminescent element 30 is formed on the first major surface 20*a* of the oxygen impermeable support layer 20, and then (D) applying the layer of pressure-sensitive adhesive 40 onto the first major surface 20*a* of the oxygen impermeable support layer 20 using conventional coating techniques after the cocktail has dried.

Generally, the concentration of the carrier polymer 32 in the organic solvent (not shown) should be in the range of 0.1 to 20% w/w, with the ratio of dye 31 to polymer 32 in the range of 1:20 to 1:10,000 w/w, preferably 1:50 to 1:5,000 w/w.

Use

The probe 10 can be used to quickly, easily, accurately and reliably measure oxygen concentration within an enclosed space S without requiring placement of the probe 10 within the enclosed space S. Briefly, the probe 10 is used to measure oxygen concentration within an enclosed space (not shown) by (A) adhering the probe 10 to the exterior surface of the membrane M forming the enclosed space S with the first major surface 20*a* of the support layer 20 facing towards the membrane M as depicted in FIGS. 4 and 5, (B) allowing the oxygen concentration in sensible communication with the oxygen-sensitive photoluminescent element 30 to equilibrate with the oxygen concentration within the space S, and (C) ascertaining oxygen concentration within the enclosed space S by (i) repeatedly exposing the probe 10 to excitation radiation over time, (ii) measuring radiation emitted by the excited probe 10 after at least some of the exposures, (iii) measuring passage of time during the repeated excitation exposures and emission measurements, and (iv) converting at least some of the measured emissions to an oxygen concentration based upon a known conversion algorithm. Such conversion algorithms are well know to and readily developable by those with routine skill in the art.

In a similar fashion, the probe 10 can be used to quickly, easily, accurately and reliably monitor changes in oxygen concentration within an enclosed space S without requiring placement of the probe 10 within the enclosed space S. Briefly, the probe 10 is used to monitor changes in oxygen concentration within an enclosed space S by (A) adhering the probe 10 to the exterior surface of the membrane M with the first major surface 20*a* of the support layer 20 facing towards the membrane M as depicted in FIGS. 4 and 5, (B) allowing the oxygen concentration in sensible communication with the oxygen-sensitive photoluminescent element 30 to equilibrate with the oxygen concentration within the space S, (C) ascertaining oxygen concentration within the enclosed space S over time by (i) repeatedly exposing the probe 10 to excitation radiation over time, (ii) measuring radiation emitted by the excited probe 10 after at least some of the exposures, (iii) measuring passage of time during the repeated excitation exposures and emission measurements, and (iv) converting at least some of the measured emissions to an oxygen concentration based upon a known conversion algorithm, and (D) reporting at least one of (i) at least two ascertained oxygen concentrations and the time interval between those reported concentrations, and (ii) a rate of change in oxygen concentration within the enclosed space calculated from data obtained in step (C). Again, conversion algorithms used to convert the measured emissions to an oxygen concentration are well know to and readily developable by those with routine skill in the art.

The radiation emitted by the excited probe 10 can be measured in terms of intensity and/or lifetime (rate of decay, phase shift or anisotropy), with measurement of lifetime generally preferred as a more accurate and reliable measurement technique when seeking to establish oxygen concentration via measurement of the extent to which the dye 31 has been quenched by oxygen.

I claim:

1. A method for transmembrane measurement of the oxygen concentration within a space enclosed by a membrane, comprising the steps of:
   (a) obtaining a transmembrane photoluminescent oxygen probe comprising at least (i) a transmembrane photoluminescent oxygen probe comprising an oxygen impermeable support layer carrying a spot of an oxygen-sensitive photoluminescent dye and a layer of a pressure-sensitive adhesive on a first major surface,
   (b) adhering the probe to the exterior surface of the membrane with the first major surface of the probe facing towards the membrane,
   (c) allowing the oxygen concentration in sensible communication with the spot of oxygen-sensitive photoluminescent dye to equilibrate with the oxygen concentration within the space, and
   (d) ascertaining oxygen concentration within the enclosed space by: (i) repeatedly exposing the equilibrated probe to excitation radiation over time, (ii) measuring radiation emitted by the excited probe after at least some of the exposures, (iii) measuring passage of time during the repeated excitation exposures and emission measurements, and (iv) converting at least some of the measured emissions to an oxygen concentration based upon a known conversion algorithm.

2. The method of claim 1 wherein the oxygen impermeable support layer on the transmembrane photoluminescent oxygen probe has an oxygen transmission rate of less than 0.1 cm$^3$/m$^2$ day.

3. The method of claim 1 wherein the layer of pressure-sensitive adhesive on the transmembrane photoluminescent oxygen probe is less than 0.8 mm thick.

4. The method of claim 1 wherein (i) the adhesive layer on the transmembrane photoluminescent oxygen probe has a peripheral edge, (ii) the spot of oxygen-sensitive photoluminescent dye on the transmembrane photoluminescent oxygen probe has a peripheral edge, and (iii) the probe has a peripheral margin of at least 2 mm from the peripheral edge of the spot of oxygen-sensitive photoluminescent dye to the peripheral edge of the adhesive layer that completely surrounds the spot of oxygen-sensitive photoluminescent dye.

5. The method of claim 1 wherein the space is a retention chamber of a hermetically sealed package containing an oxygen labile pharmaceutical or foodstuff.

6. A method for monitoring changes in oxygen concentration within a space enclosed by a membrane, comprising the steps of:
   (a) obtaining a transmembrane photoluminescent oxygen probe comprising at least (i) a transmembrane photoluminescent oxygen probe comprising an oxygen impermeable support layer carrying a spot of an oxygen-sensitive photoluminescent dye and a layer of a pressure-sensitive adhesive on a first major surface, (b) adhering the probe to the exterior surface of the membrane with the first major surface of the probe facing towards the membrane, (c) allowing the oxygen concentration in sensible communication with the spot of oxygen-sensitive photoluminescent dye to equilibrate with the oxygen concentration within the space, (d) ascertaining oxygen concentration within the space over time by: (i) repeatedly exposing the equilibrated probe to excitation radiation over time, (ii) measuring radiation emitted by the excited probe after at least some of the exposures, (iii) measuring passage of time during the repeated excitation exposures and emission measurements, and (iv) converting at least some of the measured emissions to an oxygen concentration based upon a known conversion algorithm, and (e) reporting at least one of (i) at least two ascertained oxygen concentrations and the time interval between those reported concentrations, and (ii) a rate of change in oxygen concentration within the enclosed space calculated from data obtained in step (d).

7. The method of claim 6 wherein the oxygen impermeable support layer on the transmembrane photoluminescent oxygen probe has an oxygen transmission rate of less than 0.1 $cm^3/m^2$ day.

8. The method of claim 6 wherein the layer of pressure-sensitive adhesive on the transmembrane photoluminescent oxygen probe is less than 0.8 mm thick.

9. The method of claim 6 wherein (i) the adhesive layer on the transmembrane photoluminescent oxygen probe has a peripheral edge, (ii) the spot of oxygen-sensitive photoluminescent dye on the transmembrane photoluminescent oxygen probe has a peripheral edge, and (iii) the probe has a peripheral margin of at least 2 mm from the peripheral edge of the spot of oxygen-sensitive photoluminescent dye to the peripheral edge of the adhesive layer that completely surrounds the spot of oxygen-sensitive photoluminescent dye.

10. The method of claim 6 wherein the space is a retention chamber of a hermetically sealed package containing an oxygen labile pharmaceutical or foodstuff.

* * * * *